US009579046B2

(12) United States Patent
Davydov et al.

(10) Patent No.: US 9,579,046 B2
(45) Date of Patent: Feb. 28, 2017

(54) METHOD AND APPARATUS FOR UNAMBIGUOUSLY DETERMINING ORIENTATION OF A HUMAN HEAD IN 3D GEOMETRIC MODELING

(71) Applicant: Albert Davydov, Forest Hills, NY (US)

(72) Inventors: Albert Davydov, Forest Hills, NY (US); Peter Usov, Belle Mead, NJ (US)

(73) Assignee: Albert Davydov, Forest Hills, NY (US)

( * ) Notice: Subject to any disclaimer, the term of this patent is extended or adjusted under 35 U.S.C. 154(b) by 26 days.

(21) Appl. No.: 14/808,880

(22) Filed: Jul. 24, 2015

(65) Prior Publication Data

US 2017/0020412 A1    Jan. 26, 2017

(51) Int. Cl.
*A61B 5/11*    (2006.01)
*A61B 5/00*    (2006.01)

(52) U.S. Cl.
CPC .......... *A61B 5/1114* (2013.01); *A61B 5/0077* (2013.01); *A61B 5/6803* (2013.01)

(58) Field of Classification Search
None
See application file for complete search history.

(56) References Cited

U.S. PATENT DOCUMENTS

| | | | | |
|---|---|---|---|---|
| 2007/0183567 A1* | 8/2007 | Rotondo | ................. | A61B 6/08 378/38 |
| 2012/0010533 A1* | 1/2012 | Arnett | ................. | A61B 5/0064 600/590 |
| 2012/0257162 A1* | 10/2012 | Encaoua | ............... | G02C 13/005 351/204 |
| 2014/0146132 A1* | 5/2014 | Bagnato | ............. | G02B 27/2228 348/36 |
| 2014/0275893 A1* | 9/2014 | Booker | ................. | A61B 5/684 600/340 |
| 2014/0294273 A1* | 10/2014 | Jaisson | ................ | A61B 5/7425 382/131 |
| 2016/0070110 A1* | 3/2016 | Ushakov | ................ | G08C 17/02 348/373 |

\* cited by examiner

*Primary Examiner* — Michelle Hausmann
(74) *Attorney, Agent, or Firm* — Anna Vishev, Esq.

(57) ABSTRACT

A method and apparatus for determining a three-dimensional orientation of a human head. The method includes first interposing a left and a right anthropological baselines on a patient's face, each anthropological baseline connecting an orbitale point and an auricular point on a corresponding side of the patient's face. A headgear unit having a pair of temple elements and a from housing rotatably attached to the temple elements, where the front housing includes at least two cameras and a 3D compass all movable within the front housing, is then positioned on a patient's head. Each of the two cameras is adjusted such that its view field picks up one of the two anthropological baselines on the patient's face. These view fields of the two cameras are then used to construct a Human Skull Base Plane as a plane formed by the left and right anthropological baselines when these anthropological baselines are parallel and aligned. The 3D compass is then positioned into a measuring plane coinciding with the Human Skull Base Plane, and is used to quantitatively measure a three-dimensional orientation of the patient's head at the time when the 3D compass is positioned within the measuring plane coinciding with the constructed Human Skull Base Plane.

8 Claims, 6 Drawing Sheets

METHOD AND APPARATUS FOR UNAMBIGUOUSLY DETERMINING ORIENTATION OF A HUMAN HEAD IN 3D GEOMETRIC MODELING

BACKGROUND OF THE INVENTION

This application and its disclosure generally relate to the field of determining orientation of a human head in three-dimensional geometric modeling.

Head orientation measurements in 3D geometric modeling are currently based on a combination of measurements determined by different gyroscopes, accelerometers and electronic compasses. For example, one such system is based on measurements provided by a three-axis accelerometer and a resonator gyroscope mounted on a headgear.

Other methods and measuring systems, currently in use, utilize dual inclinometers, bubble goniometers, radiographs, compass technology, visual estimation, ultrasound, geometric methods, digital optoelectronic instruments, computerized kinematic analysis using passive markers and infrared TV cameras, MRI or sensors attached to the subject's head for head orientation determination. However, none of the existing methods yield a sufficient accuracy in defining the neutral position of a human head in three-dimensions.

This lack of a precise definition of the neutral position of the 3D orientation of the human head is a serious disadvantage in current 3D geometric modeling, especially when one needs to determine some specific measurements and orientation of the human head during motion. In certain applications, for example in dental arts, the existing methods result in significant errors and distortions in the subject's measurements and, consequently, in the resulting 3D model.

SUMMARY OF THE INVENTION

It is an object of the present invention to provide an apparatus capable of performing head motion and orientation measurements that is accurate, reliable, user-friendly and portable with low-cost.

It is also an object of the present invention to provide a head-mounting apparatus allowing its user to perform correct initial installation of sensors utilizing the presently disclosed method while avoiding ambiguous orientation of the human head in 3D geometric modeling.

It is also an object of the present invention to provide a head-mounting apparatus allowing its user to measure various ranges of motion of the cervical spine of the subject.

In its general aspect, the invention is an apparatus for determining a three-dimensional orientation of a human head. The apparatus includes a headband positionable on a patient's head, a pair of temple elements, each temple element being secured to the headband, and a front housing rotatably attached to the temple elements. The front housing has at least two cameras, each of the two cameras being positioned within the front housing such that its view field picks up one of two anthropological baselines interposed onto a patient's face and connecting an orbitale point and an auricular point on one side of the patient's head. Further, the front housing includes a 3D compass positionable into a measuring plane coinciding with a Human Skull Base Plane to quantitatively measure a three-dimensional orientation of the patient's head.

In another general aspect, the invention is a method for determining a three-dimensional orientation of a human head. The method includes first interposing a left and a right anthropological baselines on a patient's face, each anthropological baseline connecting an orbitale point and an auricular point on a corresponding side of the patient's face. A headgear unit having a pair of temple elements and a front housing rotatably attached to the temple elements, where the front housing includes at least two cameras and a 3D compass all movable within the front housing, is then positioned on a patient's head. Each of the two cameras is adjusted such that its view field picks up one of the two anthropological baselines on the patient's face. These view fields of the two cameras are then used to construct a Human Skull Base Plane as a plane formed by the left and right anthropological baselines when these anthropological baselines are parallel and aligned. The 3D compass is then positioned into a measuring plane coinciding with the Human Skull Base Plane, and is used to quantitatively measure a three-dimensional orientation of the patient's head at the time when the 3D compass is positioned within the measuring plane coinciding with the constructed Human Skull Base Plane.

BRIEF DESCRIPTION OF THE DRAWINGS

The invention is illustrated by way of examples which are not a limitation, and the figures of the accompanying drawings in which references denote corresponding parts, and in which.

DETAILED DESCRIPTION OF THE INVENTION

As illustrated in the attached Figures, the method and apparatus of the present invention are used to determine a correct neutral position of the 3d orientation of a human head. Once such correct neutral position is determined, it can be used for an unambiguous definition of the 3D orientation of the human head and for head orientation during motion.

Figure 2:
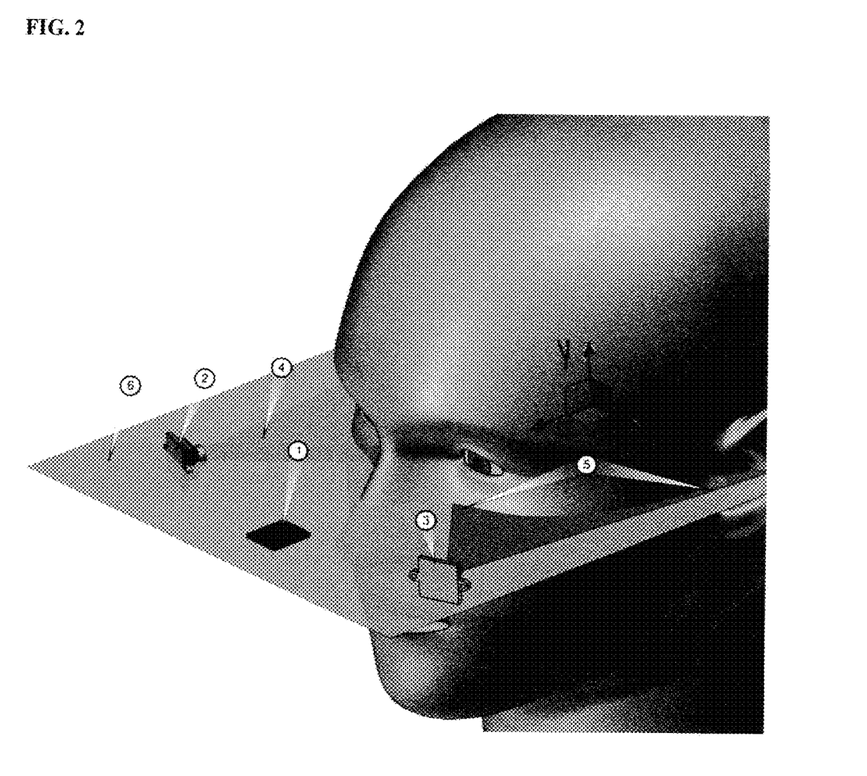
FIG. 2 is a schematic diagram of the geometric principles applicable to the present invention.
Figure 3:
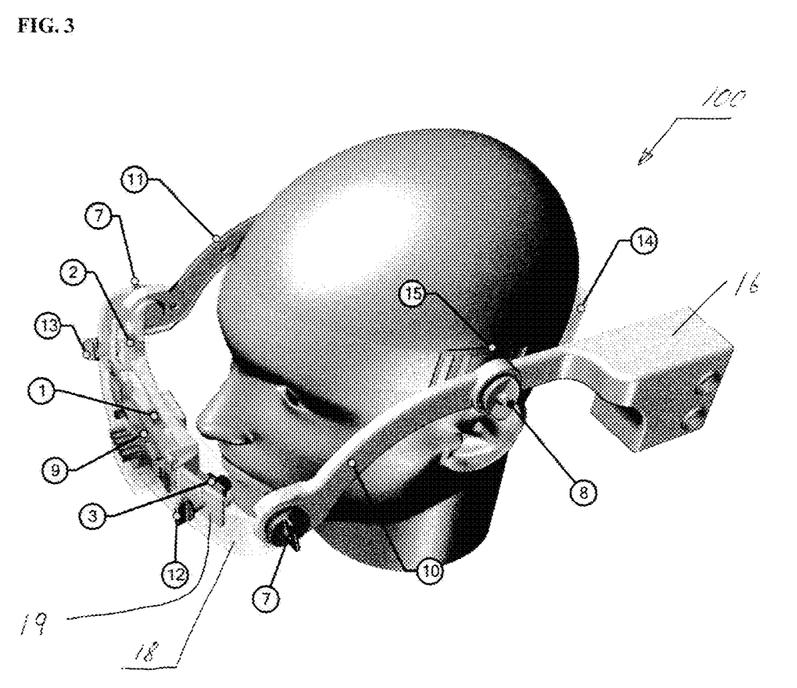
FIG. 3 is a schematic diagram of the apparatus for unambiguously determining orientation of a human head in 3d geometric modeling in accordance with one embodiment of the present invention.

Elements of the apparatus for determining the correct neutral position of the 3d orientation of human head are shown in FIGS. 2-3. In accordance with the preferred embodiment, the headgear unit 100 has a plastic frame 16 with two temple elements 10, 11 and a front housing 18. At least one 3D compass 1 with its electronic hardware 9 are secured within the front housing 18. The 3D compass 1 is an integrated compass module for heading computation and calibration of magnetic distortions. The module combines 3-axis magneto-resistive sensors and 3-axis micro electro-mechanical systems accelerometers, analog and digital support circuits. This set of compasses is intended to measure magnetic fields. A more detailed description of the compass components is provided below with respect to FIG. 4.

The headgear unit 100 further includes an adjustable headband 14 positionable on a patient's head. Frame 16 is secured to the headband 14 through clips 15 and pivot posts 8 located on each side of the headband. The frame is secured in such a way that it pivots on the posts 8 under friction with respect to the headband. Both clips 15 and pivot posts 8 can be provided in various sizes to accommodate different head sizes.

The front housing 18 also includes at least one pair of cameras, i.e., the left camera 2 and a right camera 3. The entire unit 100 can tilt slightly up or down to align the right and left cameras with the anthropological base lines. The horizontal positioning of each camera can also be adjusted and fixed using pivotable knobs 12 and 13 securing the cameras to the front housing 18. Pivotable knobs 12 and 13 are movable along the slots 19 (more clearly shown in FIG. 5). Thus, to adjust the horizontal positioning of each camera, the user will loosen the corresponding knob without detaching it from the camera, move the knob with the camera into a new desired position, and then screw the knob into place fixing the camera in the new position. Further, the entire front housing is attached to the temple elements 10, 11 with frontal knobs 7 allowing the front housing 18 with its cameras 2, 3 and 3D compass 1 to move with respect to the temple elements and without changing the position of such temple elements.

Figure 5:
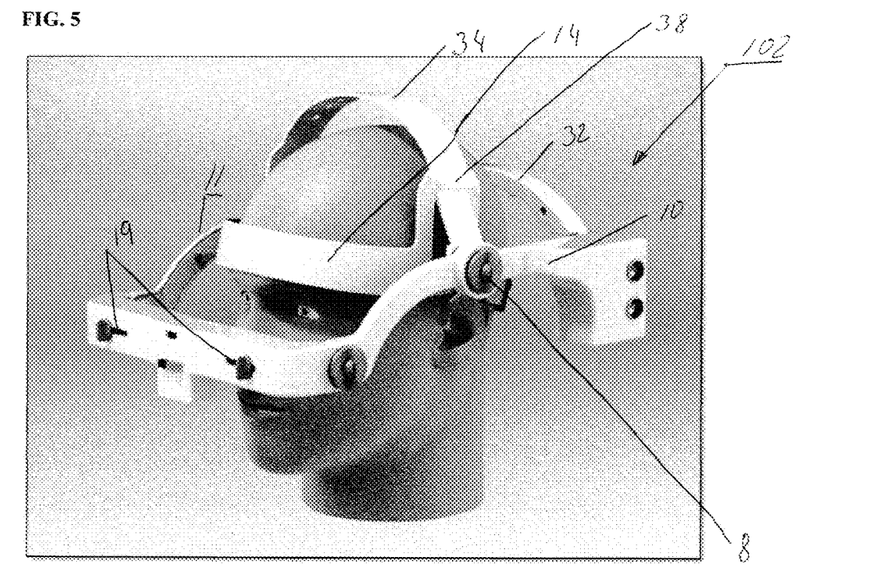
FIG. 5 is a schematic diagram of a first alternative embodiment of the headgear apparatus.
Figure 6:
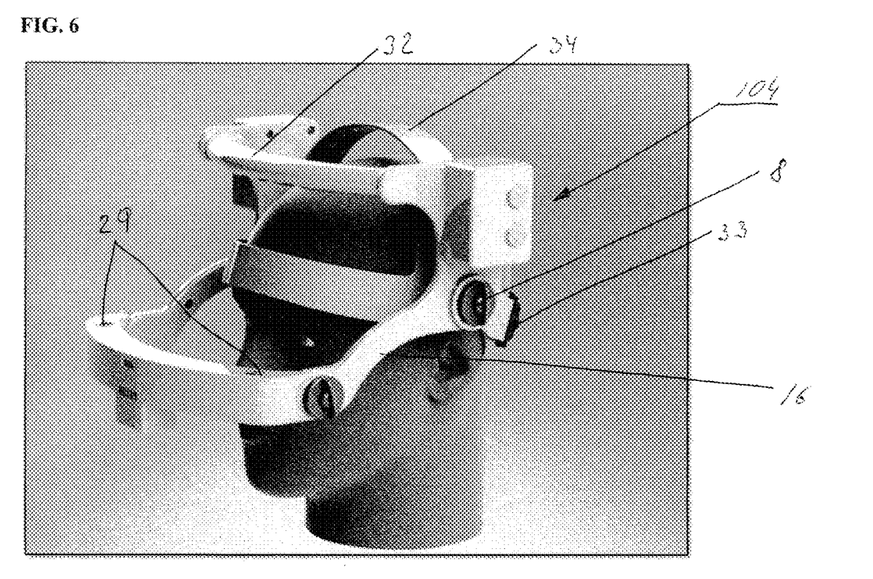
FIG. 6 is a schematic diagram of a second alternative embodiment of the headgear apparatus.
Figure 7:
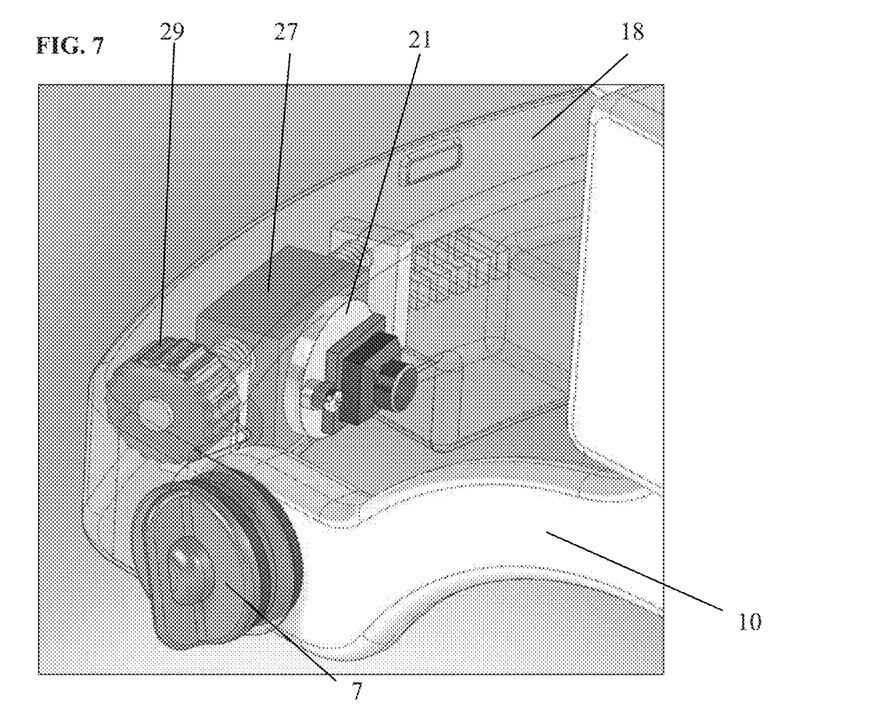
FIG. 7 is a schematic diagram of a portion of the headgear apparatus.
Figure 8:
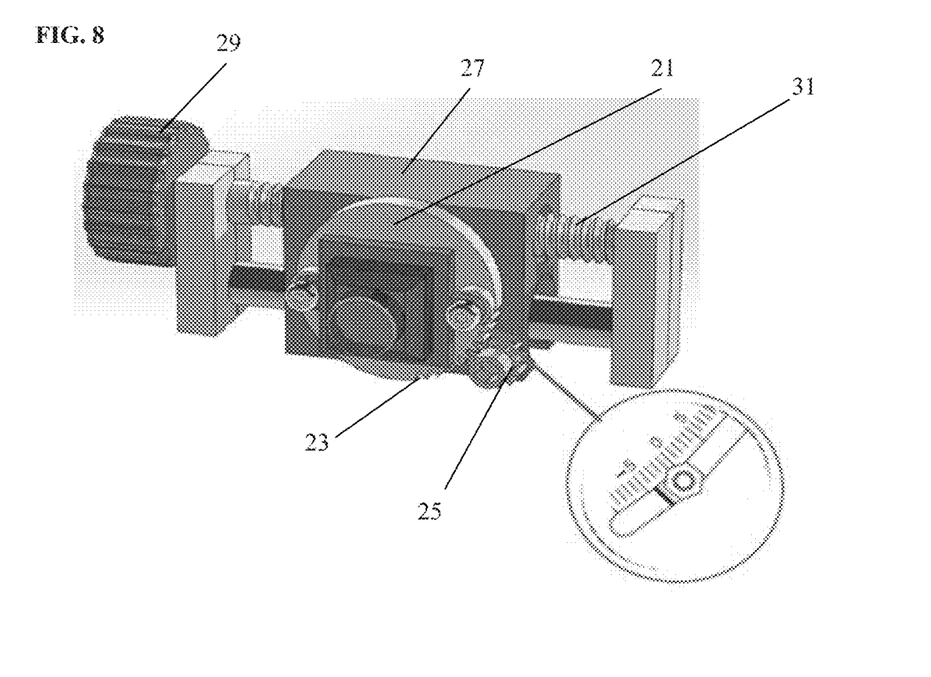
FIG. 8 is a schematic diagram of the camera mounting of the headgear apparatus.

Two alternative embodiments of the headgear apparatus are shown in FIGS. 5 and 6. As shown in FIG. 5, in addition to the elements described above with respect to headgear unit 100, headgear unit 102 includes a first arched component 32, connecting the end portions of the temple elements 10 and 11, and a second arched component 34, connected to both temple elements in the region of the pivot posts 8 and forming a part of the headband 14. Headband 14, in this embodiment (as well as in the embodiment shown in FIG. 6), includes a pair of support portions 38, extending over the second arched component 34 so as to attach and support the headband on the second arched component As shown in FIG. 6, headgear unit 104, in accordance with the second alternative embodiment, also includes the first arched component 32 and the second arched component 34. In this embodiment, however, first arched component 32 is positioned above the patient's head, and temple elements 10 and 11 are shortened. The headband 14 is secured on the patient's head with a clip 33. The entire frame 16 is pivotable around pivot posts 8 to adjust the angular position of the frame with respect to the headband and the patient's head. This embodiment provides more comfort for the patient and easier accessibility for the technician. Additionally, in this embodiment, cameras are secured differently within the front housing 18. The mechanism for securing the cameras within the front housing is more particularly shown in FIGS. 7-8. Each camera is preferably secured to a disk 21 having a set of teeth 23 connected to a gear 25. By rotating the gear 25, the user can adjust the angular position of the disk and, consequently, of the corresponding camera. Further, the disk is preferably positioned on a movable base 27. Screws 29 with their posts 31 have a worm-type connection with the movable base 27 such that, when the screw head is rotated, the movable base moves horizontally along the post 31. As shown in FIG. 6, a portion of the screw head of each screw 29 preferably protrudes above the top surface of the front housing 18. Thus, to adjust the horizontal positioning of the camera, a user will rotate the corresponding screw head, moving the corresponding base 27 into a desired position. This embodiment allows the user to adjust the horizontal positioning of the cameras in very small incremental steps, thus, resulting in higher accuracy of the measurements.

Figure 4:
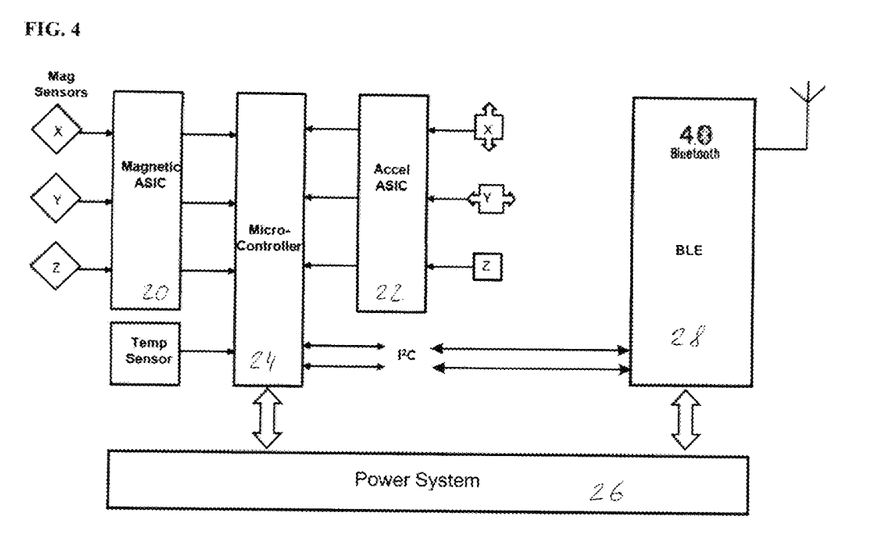
FIG. 4 is a schematic diagram of the electronic components of the 3d compass.

The electronic components of the hardware 9 are shown in FIG. 4. In accordance with the preferred embodiment, the electronic hardware includes a plurality of sensors, i.e., the 3-axis magnetic sensors 20 and 3-axial accelerometer 22, a microcontroller 24 connected to and receiving signals from the sensors 20 and 22, a power system 26 (e.g., a battery) powering all the components of the hardware, and an RF transceiver module 28.

Microcontroller 24 is integrated for computation of direction and calibration of signals from 3D compass sensors 20 and 22. It provides solid-state construction with very low cross-axis sensitivity designed to measure both direction and magnitude of Earth's magnetic fields. Power system 26 provides power to all components. With power supply applied, the sensors convert any incident magnetic field in the sensitive axis direction to a differential voltage output. RF transceiver module 28 (designated as BLE 4.0 Bluetooth® in FIG. 4) is preferably a low-power 2.4 GHz Bluetooth® 4.0 (BLE) System-on-Chip as a single mode Bluetooth Smart module that complies with Bluetooth Core Specification v4.1. It integrates RF, a baseband controller, command API processor that implements the Bluetooth Generic Attribute Profile.

Data generated by the 3D compass with its electronic hardware is a processed data that can be transmitted to any computing device, preferably wirelessly, for further processing and/or displaying on a monitoring screen. In the preferred embodiment, the 3D compass with its electronic hardware is wirelessly connected to a personal computer software using an energy-efficient reliable data transfer protocol, thereby limiting the potential errors and default settings. Furthermore, the personal computer software is able to display specific instructions to the user, in order to insure proper measurement techniques and to limit inter-user errors.

Figure 1:
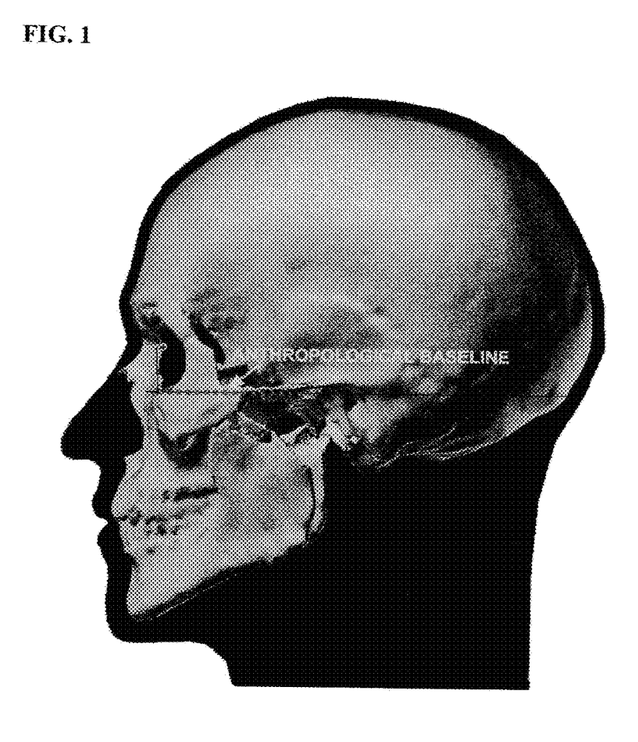
FIG. 1 is a schematic diagram of a human skull showing the anthropological baseline.

In accordance with the preferred method of the present invention the 3D compass is installed into the horizontal plane perpendicular to the sagittal plane and is rotated until the horizontal plane of the sensor is parallel to and aligned with the Human Skull Base Plane. The Human Skull Base Plane is a plane passing through the left and right anthropological baselines of a human skull. As shown in FIG. 1, the anthropological baseline as a line drawn from the inferior margin of the orbit (Orbitale point) to the auricular point (center of the orifice of the external acoustic meatus, Auricular point) and extending backward to the center of the occipital bone. In accordance with the preferred embodiment of the present invention, the left and right anthropological baselines are actually drawn on the patient's face to be picked up by the cameras. However, any other known technique for interposing the line onto the patient's face may be utilized, e.g., connecting the orbitale point to the auricular point with a ray of light projected onto the face.

The following are the geometric principles of the present method of determining a neutral position of 3D orientation of a human head. The 3D compass 1 in accordance with its predetermined algorithm is placed into the horizontal plane created perpendicular to the sagittal plane of the human head and is rotated until this horizontal plane is parallel to and aligned with the Human Skull Base Plane 6. The correct position of the compass 1 is controlled by the two cameras 2 and 3 located on the left and on the right sides, respectively. As shown in FIG. 2, each camera is placed perpendicular to the Human Skull Base Plane 6 and such that cameras' view angles 5 and 4 pick up the left and right anthropological baselines interposed on the patient's face. The cameras then digitize the signals and transmit them to a video monitor (not shown). When the picked up images of the two anthropological baselines are parallel and aligned, the plane passing through the two lines is the Human Skull Base Plane 6.

If images of the anthropological baselines of human skull on the video monitor run parallel to the X-axis and lie on the same line, then cameras 2 and 3 are set correctly. The 3D compass 1 lies on the plane perpendicular to the (vertical) Y-axis of cameras and lies in the same plane as the Human Skull Base Plane 6. This plane of the 3D compass is referred to as the measuring plane, and the position of the 3D compass 1 in this measuring plane is recorded as the correct neutral position of the patient's 3D head orientation.

As explained above, the present invention provides a computational model for determining a correct neutral position of 3D human head orientation. When the 3D compass 1 is oriented and mounted along the Human Skull Base Plane 6, the signal from the compass sensor is preferably transferred to a computer system which records this neutral position. Each movement of the patient's head thereafter is recorded and measured as relative to the recorded neutral position. Thus, all further 3D motions and orientations of the patient's head are measured with respect to an objective, neutral and independent parameter, allowing for further 3D modeling. Moreover, once the neutral position of a human skull is determined, by placing sensors on other body parts, positions and parameters of these other body parts can be accurately measured with respect to the determined neutral parameters (i.e., the anthropological baseline). For example, by placing additional sensors on a cervical spine of the patient, and recording the positions of such sensors with respect to the neutral position determined by the 3D compass, it is possible to measure various ranges of motion of the cervical spine of the patient. Based on an empirical study, the method and system of the present invention allow its user to make measurements with resulting accuracy of approximately 0.5°.

The accurate 3D modeling based on the method described herein is particularly advantageous in the following industries:

Dentistry, Orthodontics
Dentistry, Prosthodontics
Dentistry, Maxillofacial Surgery
Robotic Geriatric Patient Care
Robotic Surgical/Treatment Assistant
Robotic Surgery
General Radiology
Radiation Oncology
Physical Medicine and Rehabilitation: Orthopedic Rehabilitation Devices for Spinal Column
Toys and Video Games
Aero Space and Machinery Operators Training Systems
Imitation of Disaster Situations and Training for their Mitigations (Accidents, car accidents, etc.)
Simulation Systems of Human Body
Human Body LPS (Local Position System)
High Precision Military Robotic Systems
High Accuracy Head Based Aiming Systems
Dentistry, TMJ Metric Analysis
Dentistry, TMJ orthotics and
Sleep Apnea Appliances planning and fabrication In the preceding specification, the invention has been described with reference to specific exemplary embodiments thereof. It will however, be evident that various modifications and changes may be made thereto without departing from the broader spirit and scope of the invention as set forth in the claims that follow. The specification and drawings are accordingly to be regarded in an illustrative manner rather than a restrictive sense.

We claim as follows:

1. An apparatus for determining a three-dimensional orientation of a human head, the apparatus comprising:
    a headband positionable on a patient's head;
    a pair of temple elements, each temple element being secured to the headband; and
    a front housing rotatably attached to said temple elements, said front housing including at least two cameras, each of said two cameras being positioned within said front housing such that its view field picks up one of two anthropological baselines interposed onto a patient's face and connecting an orbitale point and an auricular point on one side of the patient's head, said front housing further comprising a 3D compass configured to be positioned into a measuring plane coinciding with a plane formed by said two anthropological baselines when said two baselines are parallel and aligned, said 3D compass being further configured to quantitatively measure a three-dimensional orientation of the patient's head when said 3D compass is positioned in said measuring plane.

2. The apparatus according to claim 1, wherein said 3D compass comprises at least one three-axial magnetic sensor, at least one three-axial accelerometer, a microcontroller connected to and receiving signals from said sensor and said accelerometer, a transceiver module transmitting and receiving data signals to and from said 3D compass, and a power system.

3. The apparatus according to claim 1, wherein each of said two cameras is fixedly secured to a disk having a set of teeth and connected to a gear, such that rotation of said gear adjusts an angular position of said disk and a corresponding camera.

4. The apparatus according to claim 1, wherein each of said two cameras is attached to a movable base such that a movement of said movable base changes a horizontal position of a corresponding camera.

5. The apparatus according to claim 4, further comprising a screw head connected to said movable base with a worm-type connection so as to move said movable base with small incremental steps.

6. A method for determining a three-dimensional orientation of a human head, the method comprising: the steps of:
    interposing a left and a right anthropological baselines on a patient's face, each anthropological baseline connecting an orbitale point and an auricular point on a corresponding side of the patient's face;
    providing a headgear unit comprising a pair of temple elements and a front housing rotatably attached to said temple elements, said front housing including at least two cameras and a 3D compass all movable within the front housing;
    positioning the headgear unit on a patient's head;
    positioning each of said two cameras such that its view field picks up one of said anthropological baselines on the patient's face;
    using the view fields of said two cameras to construct a Human Skull Base Plane as a plane formed by said left and right anthropological baselines when said anthropological baselines are parallel and aligned;

positioning said 3D compass into a measuring plane coinciding with the constructed Human Skull Base Plane; and using said 3D compass to quantitatively measure a three-dimensional orientation of the patient's head at the time when said 3D compass is positioned within the measuring plane coinciding with the constructed Human Skull Base Plane.

7. The method in accordance with claim 6, further comprising the step of recording said measured three-dimensional orientation of the patient's head at the time when said 3D compass is positioned within the plane coinciding with the Human Skull Base Plane as a neutral position of the patient's head.

8. The method in accordance with claim 7, further comprising the steps of using said 3D compass to quantitatively measure a new three-dimensional orientation of the patient's head after said patient moves its head and quantitatively comparing said new three-dimensional orientation of the patient's head to said neutral position.

* * * * *